United States Patent [19]

Maeda et al.

[11] Patent Number: 5,268,366
[45] Date of Patent: Dec. 7, 1993

[54] POLYSACCHARIDE COMPOSITION OR POLYSACCHARIDE HAVING HEPARINOID ACTIVITY, PROCESS FOR PRODUCING THE SAME, AND ANTICOAGULANT CONTAINING THE SAME AS ACTIVE INGREDIENT

[75] Inventors: Masaakira Maeda; Tsutomu Uehara, both of Saitama; Masao Takeshita, Chiba, all of Japan

[73] Assignee: Nisshinbo Industries, Inc., Tokyo, Japan

[21] Appl. No.: 757,786

[22] Filed: Sep. 11, 1991

[30] Foreign Application Priority Data

Sep. 11, 1990 [JP] Japan .................. 2-241004

[51] Int. Cl.$^5$ .............. A61K 31/735; C07H 1/08; C07H 13/12; C12P 19/04
[52] U.S. Cl. ........................ 514/54; 536/54; 536/123.1; 536/124; 536/128; 435/101; 435/946
[58] Field of Search .......... 536/54, 123, 124, 128, 536/123.1; 514/54; 435/101, 946

[56] References Cited

PUBLICATIONS

Colliec et al.; Chemical Abstracts 114:124842t (1991).
Dobashi et al.; Chemical Abstracts 112:95577m (1990).
Nishino et al.; Carbohydrate Research 186:119-129 (1989).
Matulewicz et al.; Chemical Abstracts 107(9):74301y (1987).
Wakamoto; Chemical Abstracts 100:12641f (1984).
Caporiccio et al.; Chemical Abstracts 100:45075c (1984).
Yamamoto et al.; Agric. Biol. Chem. 44(4):723-729 (1980).
Yamamoto et al.; Agric. Biol. Chem. 44(3):589-593 (1980).
Yamamoto et al.; Chemical Abstracts 84:2283c (1976).
Nakazawa et al.; Chemical Abstracts 85:83151d (1976).
Yamamoto et al.; Chemical Abstracts 87:130526h (1977).
Yamamoto; Agric. Chem. Biol. 44(3):673-675 (1980).

Primary Examiner—Nancy S. Husarik
Attorney, Agent, or Firm—Shea & Gould

[57] ABSTRACT

The present invention provides 1) a polysaccharide composition and a polysaccharide both having a heparinoid activity, obtained from green algae belonging to Codiaceae of Codiales, 2) a processes for producing said polysaccharide composition and said polysaccharide, as well as 3) an anticoagulant containing, as an active ingredient, said polysaccharide composition or polysaccharide both having a heparinoid activity.

6 Claims, 4 Drawing Sheets

POLYSACCHARIDE COMPOSITION OR POLYSACCHARIDE HAVING HEPARINOID ACTIVITY, PROCESS FOR PRODUCING THE SAME, AND ANTICOAGULANT CONTAINING THE SAME AS ACTIVE INGREDIENT

BACKGROUND OF THE INVENTION
(1) Field of the Invention

The present invention relates to a polysaccharide composition or polysaccharide having heparinoid activity, obtained from green algae belonging to Codiaceae of Codiales, a process for producing said composition or polysaccharide, and a coagulant containing said composition or polysaccharide as an active ingredient.

(2) Description of the Prior Art

Substances having heparinoid activity, show an action of inhibiting coagulation of blood or an action of clearing lipid in blood. Therefore, these substances are used for remedy of various diseases. As such substances having heparinoid activity, there have hitherto been known heparin, sulfated polysaccharides such as the sodium salt of dextran sulfate and the like.

These conventional substances having a heparinoid activity, however, have drawbacks. Heparin has problems, for example, in that (1) it must be extracted from internal organs of higher animals, etc. and purified and accordingly the production is difficult and (2) the heparin obtained has a non-uniform activity; and the sodium salt of dextran sulfate has problems, for example, in production and weak heparinoid activity. Hence, it has been desired to develop and provide a novel substance having an effective heparinoid activity.

Meanwhile, it is well known that fucoidan sulfate which is obtained from brown algae and which is a polysaccharide sulfate composed mainly of L-fucose, has heparinoid activity. A rhamnan sulfate having strong heparinoid activity, obtained from green algae belonging to Monostroma genus, was found by the research based on the above knowledge and a patent application was filed therefor (Japanese Patent Publication No. 235301/1988).

Japan and some countries are completely surrounded by the sea, and algae such as green algae and the like are abundant in the sea. It is an object of the present invention to provide a polysaccharide composition or polysaccharide other than said rhamnan sulfate, having strong heparinoid activity, obtained from green algae and also to utilize the green algae effectively.

It is another object of the present invention to provide a process for producing said polysaccharide composition or polysaccharide without causing the above-mentioned problems possessed by the process for producing heparin or sodium dextran sulfate, and also to provide useful application of said polysaccharide composition or polysaccharide.

SUMMARY OF THE INVENTION

According to the present invention, there is provided a polysaccharide composition having heparinoid activity, obtained from green algae belonging to Codiaceae of Codiales. According to the present invention, there is also provided a polysaccharide having heparinoid activity and having the following physical and chemical properties:

(a) color and shape: a colorless to slightly light yellow powder (b) solubility:
  easily soluble in water and dimethyl sulfoxide
  soluble in 0 to 6N hydrochloric acid, sulfuric acid and nitric acid
  soluble in 0 to 20% ethyl alcohol
  soluble in 0 to 3N aqueous sodium hydroxide solution
  insoluble in benzene and cyclohexane (c) composition: a homopolysaccharide composed mainly of L-arabinofuranose (d) sulfuric acid ester content: 10 to 25% based on dry weight of polysaccharide (e) IR absorption spectrum: shown in FIG. 1

(f) $^1$H NMR absorption spectrum (400 MHz): shown in FIG. 2

(g) specific rotation:
  $[\alpha]^{D}{}_{25} = -15.0$ to $+15.0$

According to the present invention, there is also provided a process for producing a polysaccharide composition having heparinoid activity, which process comprising subjecting green algae belonging to Codiaceae of Codiales, to extraction with water.

According to the present invention, there is also provided a process for producing a polysaccharide having heparinoid activity, which comprises subjecting green algae belonging to Codiaceae of Codiales to extraction with water and then subjecting the extract to fractional precipitation using dilute potassium chloride to purify the extract.

According to the present invention, there is also provided an anticoagulant containing, as an active ingredient, the above-mentioned polysaccharide composition or polysaccharide having heparinoid activity.

DETAILED DESCRIPTION OF THE INVENTION

Figure 1:
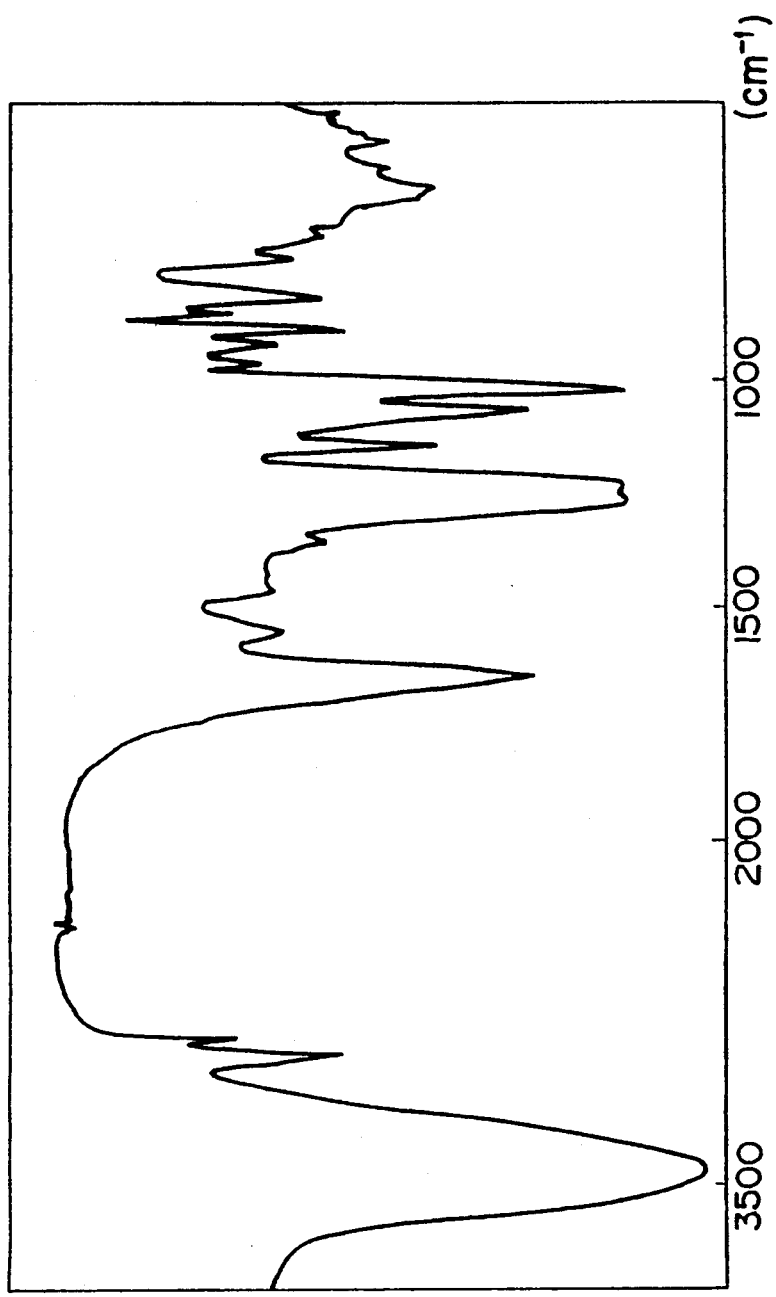
FIG. 1 is a graph showing IR absorption spectrum of polysaccharide.

The green algae used in the production of the polysaccharide having a heparinoid activity according to the present invention, are those belonging to Codiaceae of Codiales and preferably *Codium latum*. The green algae belonging to Codiaceae of Codiales, such as *Codium latum* and the like are conveniently used by drying after collection.

Incidentally, *Codium latum* is taxonomically different from *Monostroma nitidum* from which rhamnan sulfate is extracted.

In producing the polysaccharide composition or polysaccharide having a heparinoid activity, of the present invention from green algae belonging to Codiaceae of Codiales, such as *Codium latum* and the like, first *Codium latum* or the like preferably in a dried form is immersed in, for example, water for an appropriate length of time to swell it, and the mixture is stirred by a blender or the like to disintegrate the swollen algae and then is subjected to, for example, filtration by a cloth to obtain a cold water extract. The cold water extract is dialyzed against running water and the dialyzate is centrifuged, and the supernatant is freeze-dried to obtain a water-extracted crude polysaccharide which is a polysaccharide composition of the present invention.

Also, it is possible to add water to the extraction residue obtained above, heat the mixture, filter the mixture using a cloth to obtain a hot water extract, subject the hot water extract to dialysis and centrifuging, and freeze-dry the supernatant to obtain a hot water-extracted crude polysaccharide which is a polysaccharide composition of the present invention.

The polysaccharide composition of the present invention can be purified by passing the composition through a DEAEcellulose column (e.g. Whatman DE 52, OH type) with water or an aqueous sodium chloride solution used as an eluting solvent. In this case, the ionic strength of sodium chloride in the aqueous sodium chloride solution is, for example, 0.5 to 3.0M, and elution is effected by varying the ionic strength within the range stepwise or concentration gradient-wise.

The thus obtained polysaccharide composition of the present invention has heparinoid activity differing slightly depending upon the degree of purification, etc., but the heparinoid activity is appropriately 1.1 to 6.0 in terms of specific activity when the blood coagulation inhibitory activity of standard heparin is taken as 1.

The heparinoid activity is measured as follows.

A physiological saline solution containing bovine thrombin is added to a physiological saline solution containing fetal calf serum. Thereto is added a barbital buffer solution (pH 7.0), and mixing is effected and then the mixture is brought to a temperature equilibrium, using as a heparine cofactor. To the mixture is added a physiological saline solution containing fibrinogen, and there is measured a time ($T_1$ sec) taken from the moment of this addition to the formation of fibrin.

Separately, a barbital buffer solution (pH 7.0) containing a substance having heparinoid activity is added to above-mentioned physiological saline solution containing bovine thrombin and physiological saline solution containing fetal calf serum. To the mixture is added a physiological saline solution containing fibrinogen, and there is measured a time ($T_2$ sec) taken from the moment of this addition to the formation of fibrin.

A time difference (sec) is taken as an indication of blood coagulation inhibitory activity.

The above-extracted crude polysaccharide is purified to obtain a polysaccharide of the present invention. This purification may be effected by an ion exchange chromatography using a DEAE-cellulose column, as in the production of the polysaccharide composition of the present invention, but is preferably effected by fractional precipitation by dilute potassium chloride in view of the easy procedure and the activity of the polysaccharide obtained. The concentration of dilute potassium chloride in the fractional precipitation is, for example, about 0.2M.

The crude polysaccharide of the present invention may also be purified by effecting the above fractional precipitation by dilute potassium chloride and then effecting an ion exchange chromatography using a DEAE-cellulose column. The thus obtained polysaccharide having a heparinoid activity according to the present invention, is characterized by having the following physical and chemical properties.

(a) color and shape: a colorless to slightly light yellow powder (b) solubility:

easily soluble in water and dimethyl sulfoxide soluble in 0 to 6N hydrochloric acid, sulfuric acid and nitric acid soluble in 0 to 20% ethyl alcohol soluble in 0 to 3N aqueous sodium hydroxide solution insoluble in benzene and cyclohexane (c) composition: a homopolysaccharide composed mainly of L-arabinofuranose The composition was identified from the $^1$H NMR absorption spectrum, IR absorption spectrum and gas liquid chromatography of the hydrolyzate of the present polysaccharide and from the melting point of the diphenylhydrazone derivative of the hydrolyzate.

(d) sulfuric acid ester content: 10 to 25% based on dry weight of polysaccharide This content was determined by measuring the IR absorption spectrum of the polysaccharide and calculating the absorption area in the vicinity of 1,240 cm$^{-1}$ using the calibration curve obtained with chondroitin sulfate A and also by using, in combination, colorimetry using a sodium rhodizonate reagent.

(e) IR absorption spectrum: shown in FIG. 1

Figure 2:
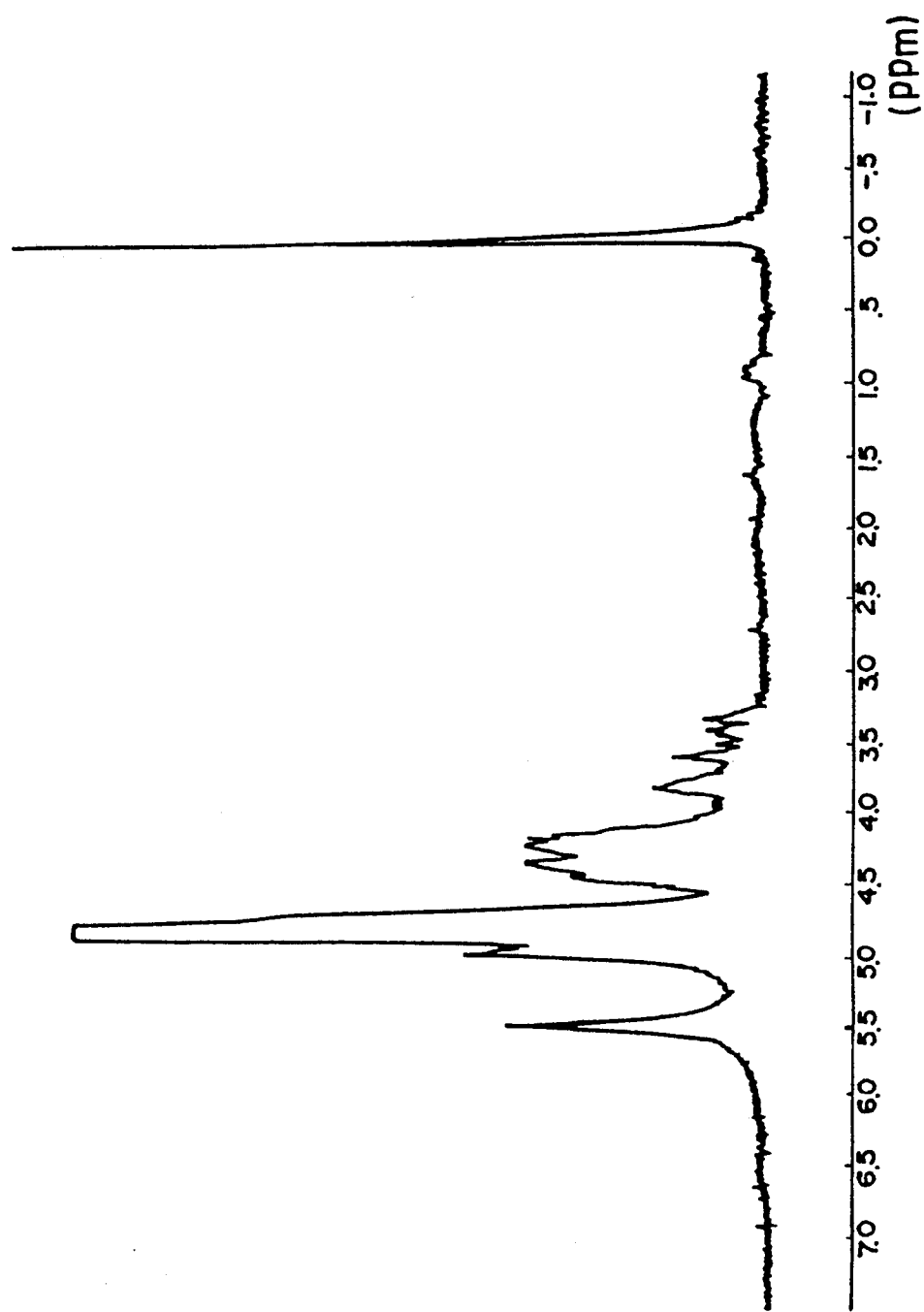
FIG. 2 is a graph showing $^1$H NMR absorption spectrum (400 MHz) of polysaccharide.

(f) $^1$H NMR absorption spectrum (400 MHz): shown in FIG. 2

(g) specific rotation: $[\alpha]^D_{25} = -15.0$ to $+15.0$

The polysaccharide of the present invention, when measured for molecular weight according to a gel filtration method after desulfation, had a molecular weight of 150,000 to 300,000.

Further, the polysaccharide of the present invention has heparinoid activity of 6.0 to 15.0 in terms of specific activity when the blood coagulation inhibitory activity of standard heparin is taken as 1.

The anticoagulant of the present invention is characterized by containing the above-mentioned polysaccharide composition or polysaccharide of the present invention as an active ingredient. The anticoagulant of the present invention can be made into a drug of appropriate form such as powder, ointment or the like similarly to the conventional heparin drugs and can be administered.

EXAMPLES

The present invention is hereinafter described in more detail by way of Examples.

1. Extraction of crude polysaccharide from *Codium latum*.

*Codium latum* was collected at Shirahama beach of Izu Peninsula, Japan. It was thoroughly washed in the sea water to remove impurities, and air-dried in a room to use as a material.

The air-dried material was immersed in distilled water of about five-fold weight for 1 hour. The mixture was stirred by a blender to disintegrate the material and then allowed to stand at room temperature for 2 hours. The mixture was filtered through a cloth to obtain a cold water extract. The cold water extract was dialyzed against running water for 3 days, the dialyzate was centrifuged and the supernatant was freeze-dried to obtain a cold water-extracted polysaccharide, i.e. a polysaccharide composition of the present invention.

The same amount of distilled water was added to the extraction residue. The mixture was heated at 100° C. for 1 hour and then filtered through a cloth to obtain a hot water extract. The hot water extract was dialyzed for 3 days, the dialyzate was centrifuged and the supernatant was freeze-dried to obtain a hot water-extracted polysaccharide, i.e. a polysaccharide composition of the present invention.

2. Measurement of blood coagulation inhibitory activity

Blood coagulation inhibitory activity was measured as an anti thrombin activity (ATA) in an in-vitro system to which a heparin co-factor has been added.

As a heparin co-factor, 1 ml of a physiological saline solution containing bovine thrombin (a product of Oriental Yeast) was added to 1 ml of a physiological saline solution containing 1% of fetal calf serum (a product of Wako Pure Chemical Industries, Ltd.). Thereto was added 2 ml of a 20 mM barbital buffer solution (a product of Wako Pure Chemical Industries, Ltd., pH 7.0), and mixing was effected. The mixture was immersed in a water bath of 37° C. for 90 minutes and brought to a temperature equilibrium.

To 0.3 ml of the mixture was added 1 ml of a physiological saline solution containing 1% of fibrinogen (a product of Japan Chemical Research), and there was measured a time ($T_1$ sec) taken from the moment of this addition to the formation of fibrin.

Separately, in a system to which 2 ml of a 20 mM barbital buffer solution (a product of Wako Pure Chemical Industries, Ltd., pH 7.0) containing heparin or a substance having heparinoid activity had been added, there was measured a time ($T_2$ sec) taken up to the formation of fibrin.

A time difference (sec) was calculated and taken as an ATA value which is an indication of blood coagulation inhibitory activity. Incidentally, there was used, as heparin, a standard product used in the standard test by The Pharmacopoea of Japan; as the time taken up to the formation of fibrin, there was taken an average value of five or more measurements; and the ATA value was obtained using 6 μg/ml of a test sample.

The cold water-extracted polysaccharide and hot water-extracted polysaccharide both obtained in the above 1. were measured for blood coagulation inhibitory activity according to the above method. As a result, the cold water-extracted polysaccharide had a higher activity than the hot water-extracted polysaccharide, and its ATA value was 2.2 when that of heparin was taken as 1. 3-1. Fractionation and purification (1) of the cold water-extracted polysaccharide It was effected by an ion exchange chromatography using a DEAE-cellulose column.

1 g of the cold water-extracted polysaccharide was dissolved in about 500 ml of water. The mixture was subjected to centrifugation. The insoluble residue was removed, and the supernatant liquid was subjected to the above column. Then, distilled water was passed through to remove the components not adsorbed by the gel. Elution by aqueous sodium chloride solution was effected by changing the ionic strength of the solution stepwise in the order of 0.5M, 1.0M, 2.0M and 3.0M.

Figure 3:
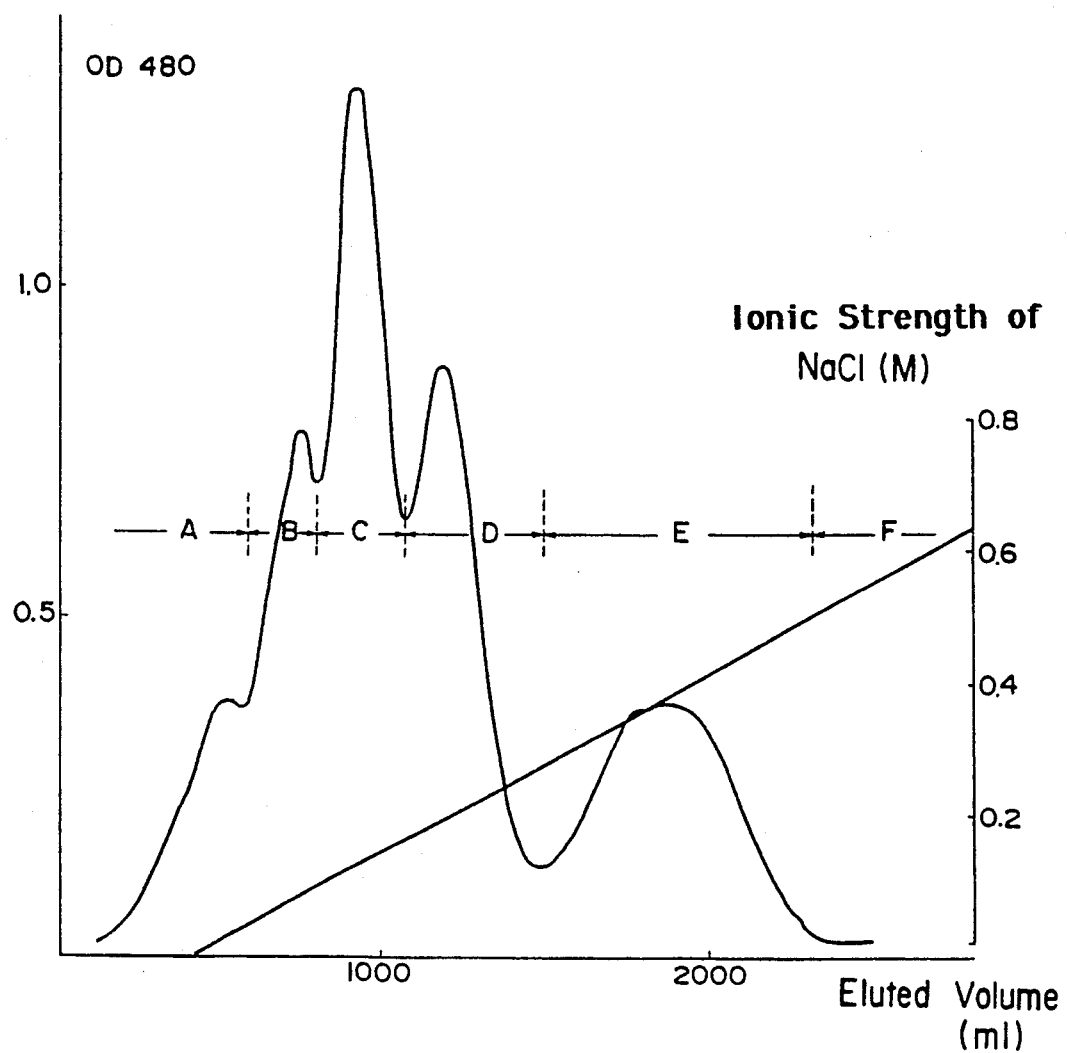
FIG. 3 is a graph showing an elution profile obtained in purification step of water-extracted polysaccharide composition by ion exchange chromatography.

The fractions obtained by the above procedure were dialyzed, centrifuged and measured for blood coagulation inhibitory activity according to the method mentioned in the above 2. The fraction obtained with a sodium chloride concentration of 0.5M gave the strongest activity (2.2 to 3.0 in terms of ATA when that of heparin was taken as 1). Hence, this fraction was subjected again to an ion exchange chromatography, and then elution by aqueous sodium chloride solution was effected by changing the concentration of the solution gradient-wise, to obtain an elution profile as shown in FIG. 3.

Each of the fractions obtained was measured for blood coagulation inhibitory activity according to the method mentioned in the above 2. The fraction E shown in FIG. 3 gave the strongest activity. The activity of the polysaccharide of the present invention contained in this fraction E was 5.6 in terms of ATA value when that of standard heparin was taken as 1.

3-2. Analysis of monosaccharides as constituents

Each polysaccharide obtained in each step above was hydrolyzed with 2N sulfuric acid, followed by analysis by gas chromatography. The monosaccharides constituting each polysaccharide were confirmed to be large amounts of L-arabinofranose and slight amounts of D-galactose, by their comparison with respective standard products. It was also confirmed that in the polysaccharides obtained in each step, the volume proportion of D-galactose decreased and the volume proportion of L-arabinofuranose increased as the purification proceeded. 4-1 Fractionation and purification (2) of the cold water-extracted polysaccharide This was effected by a fractional precipitation using dilute potassium chloride. Dilute potassium chloride was added to the cold water-extracted polysaccharide; the mixture was subjected to centrifugation; the resulting precipitate showed an increase in blood coagulation inhibitory activity but the supernatant liquid showed no blood coagulation inhibitory activity; therefore, a fractional precipitation using a dilute potassium chloride was applied.

Precipitate fractions obtained with various concentrations of potassium chloride were measured for blood coagulation inhibitory activity. As a result, the precipitate fractions obtained when the dilute potassium chloride solution was added so as to give final concentrations of 0.2M to 3.0M, showed a high activity and, in particular, the precipitate fraction obtained when the dilute potassium solution was added so as to give a final concentration of 0.2M, showed the highest activity. The activity of the present polysaccharide contained in the precipitate fraction varied depending upon the final concentration of the dilute potassium chloride solution, but was 6.5 to 9.6 in terms of ATA when that of standard heparin was taken as 1.

Hereinafter, this faction is referred to as "K fraction" containing the polysaccharide of the present invention.

4-2. Chemical analysis of K fraction (1) Electrophoresis by cellulose acetate membrane A single migration zone was observed at the anode side, which indicated that a single homo polysaccharide after purification had taken place.

Therefore, the polysaccharide contained in the K fraction is the polysaccharide of the present invention.

(2) IR absorption spectrum

There was obtained a spectrum as shown in FIG. 1, in which the absorption of stretching vibration by S=O characteristic of sulfuric acid ester was seen at 1,240 cm$^{-1}$. Using this spectrum, the content of sulfate group was determined to be about 20%.

Hence, the present polysaccharide can be said to be an arabinan sulfate.

(3) $^1$H NMR absorption

A spectrum as shown in FIG. 2 was obtained.

In the spectrum, a signal of anomeric proton is seen in the vicinity of 5.5 ppm, which indicates that the polysaccharide has an α-L-configuration.

(4) Specific rotation $[\alpha]^D_{25}$ was +2.4.

(5) Gas chromatography for hydrolyzate

The hydrolyzate was converted to a trifluoroacetylalditol derivative and analyzed by a gas chromatography using a column (2 mm×100 cm) packed with 2% fluorinated silicon (column temperature: 105° C., carrier: nitrogen gas, flow rate:60 ml/min). A single peak was seen in the retention time of 5.7 minutes, and this retention time was identical with that observed for trifluoroacetylalditol derivative of L-arabinofuranose.

4-3. Configuration of monosaccharide as constituent 1,1-Diphenylhydrazone derivative of the above hydrolyzate was synthesized, and its melting point was measured. The measurement gave 183°-185° C. Meanwhile, the 1,1-diphenylhydrazone derivative of L-arabinofuranose has a melting point of 183°-185° C., and the derivative of D-arabinose has a melting point of 189°-193° C. Further, the mixture of the derivative of the hydrolyzate with the derivative of L-arabinofuranose gives a melting point of 183°-185° C., and the mixture of the derivative of the hydrolyzate with the derivative of D-arabinose showed a melting point depression. Accordingly, the monosaccharide constituting the K fraction was decided to be L-arabinofuranose.

Further, the $^1$H NMR absorption spectrum of the hydrolyzate agreed with the spectrum of a standard sample of L-arabinofuranose.

4-4. Methylation of K fraction

Figure 4:
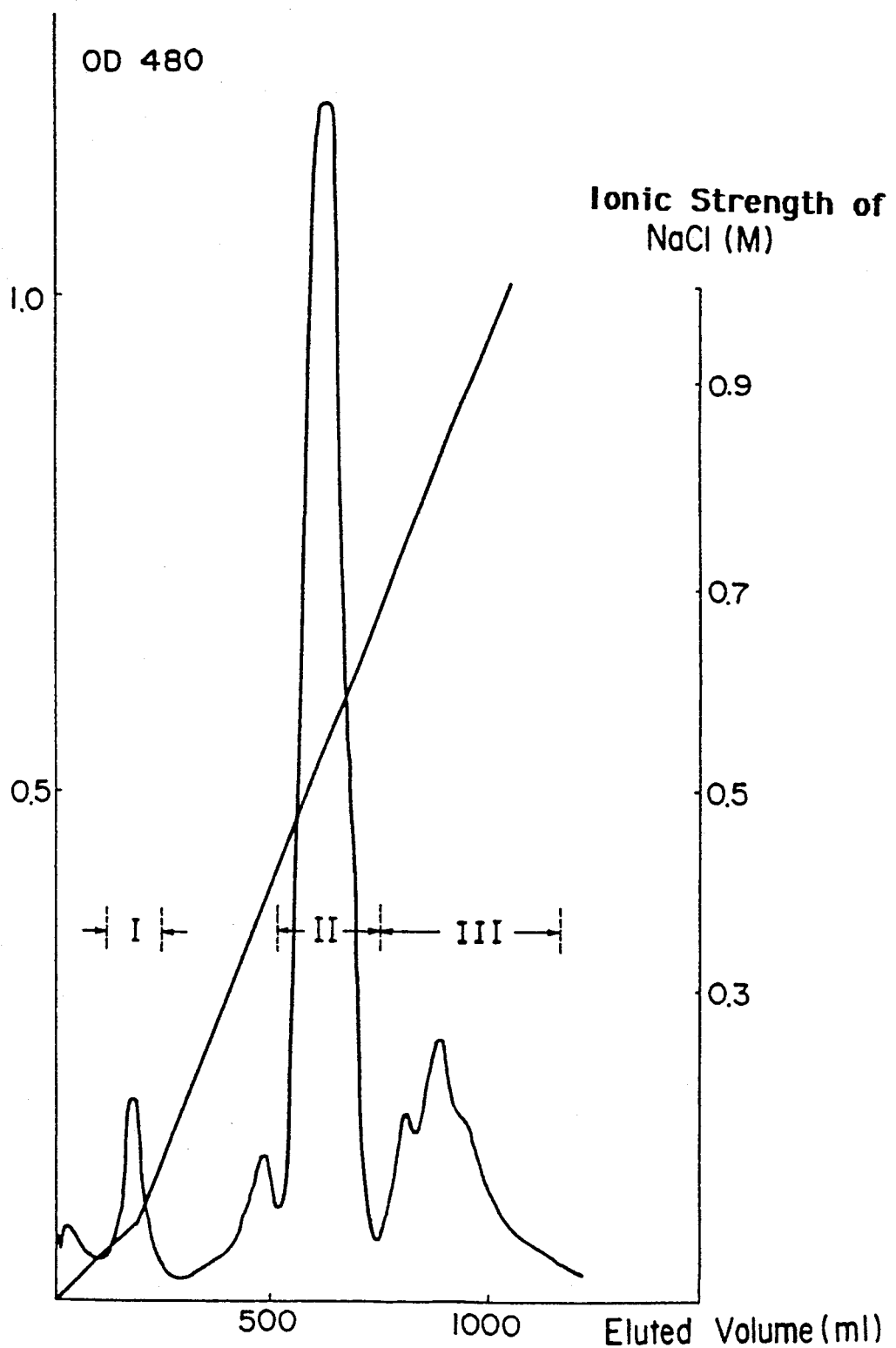
FIG. 4 is a graph showing an elution profile obtained in the purification step of K fraction by ion exchange chromatography.

The polysaccharide contained in the K fraction obtained in the above 4-1. was subjected to desulfation and then to complete methylation. Completely methylated polysaccharide was subjected to hydrolysis, followed by acetylation, and the resulting partially methylated alditol acetate was subjected to gas chromatography. As a result, two peaks were observed and the major portion of them was revealed as 2,5-di-0-methyl arabinitol by GC-MS, therefore it consisted of a furanose ring and that the polysaccharide was a straight chain polysaccharide consisting of an α-L-1,3 bond. 4-5. Measurement of molecular weight The molecular weight was measured after desulfation, by a gel filtration method. It was approximately 270,000. 4-6. Purification of K fraction The K fraction obtained in the above 4-1. was subjected to an ion exchange chromatography using DEAE-Toyopearl (a product of TOYO SODA MAG. CO., LTD.). Then, elution by aqueous sodium chloride solution was effected by changing the ionic strength of the solution gradient-wise. As a result, an elution profile as shown in FIG. 4 was obtained.

Each of the fractions obtained was measured for blood coagulation inhibitory activity according to the method mentioned in the above 2. The fraction II shown in FIG. 4 gave the strongest activity.

Incidentally, the activity of the polysaccharide contained in the fraction II was about 12.6 in terms of ATA when that of standard heparin was taken as 1.

As described above, the present invention can provide a polysaccharide composition or polysaccharide other than rhamnan sulfate (obtained from green algae belonging to Monostroma genus), which is obtained from green algae (e.g. *Codium latum*) belonging to Codiaceae of Codiales and which has strong heparinoid activity. The present invention further enables the effective utilization of said green algae.

The process of the present invention for producing said polysaccharide composition or polysaccharide is free from a problem of variation in product quality due to non-uniform sulfation, as seen in the conventional production of heparin or sodium dextran sulfate, is easy to carry out and economical. The present polysaccharide having heparinoid activity produced from said process is useful as an anticoagulant.

What is claimed is:

1. A polysaccharide having blood coagulation inhibiting activity and having the following physical and chemical properties:
    (a) color and shape: a colorless to slightly light yellow powder;
    (b) solubility:
        easily soluble in water and dimethyl sulfoxide
        soluble in 0 to 6N hydrochloric acid, sulfuric acid and nitric acid
        soluble in 0 to 20% ethyl alcohol
        soluble in 0 to 3N aqueous sodium hydroxide solution
        insoluble in benzene and cyclohexane;
    (c) composition: a homopolysaccharide consisting essentially of L-arabinofuranose;
    (d) sulfuric acid ester content: 10 to 25% based on dry weight of polysaccharide;
    (e) IR absorption spectrum: shown in FIG. 1;
    (f) $^1$H NMR absorption spectrum (400 MHz): shown in FIG. 2;
    (g) specific rotation: $[\alpha]^D{}_{25} = -15.0$ to $+15.0$; and
    (h) a molecular weight of 150,000 to 300,000 as measured by gel filtration after desulfation.

2. A polysaccharide having blood coagulation inhibiting activity according to claim 1, wherein the blood coagulation inhibiting activity is 6.0 to 15.0 when the blood coagulation inhibiting activity of standard heparin is taken as 1.

3. A process for producing a polysaccharide having blood coagulation inhibiting activity, which comprises subjecting green algae belonging to Codiaceae of Codiales, to extraction with water and then subjecting the extract to fractional precipitation using dilute potassium chloride to obtain a homopolysaccharide consisting essentially of L-arabinofuranose.

4. A process for producing a polysaccharide having blood coagulation inhibiting activity according to claim 3, wherein the green algae belonging to Codiaceae of Codiales are *Codium latum*.

5. An anticoagulant comprising, as an active ingredient, the polysaccharide of claim 1 in combination with a pharmaceutically acceptable excipient.

6. A method for inhibiting coagulation of blood in a patient requiring the inhibition of coagulation of blood comprising administering a blood coagulation inhibiting effective amount of an anticoagulant of claim 5 to said patient.

* * * * *